(12) United States Patent
Goldenberg et al.

(10) Patent No.: US 7,732,399 B2
(45) Date of Patent: *Jun. 8, 2010

(54) SUSTAINED RELEASE FORMULATIONS

(75) Inventors: Merrill S. Goldenberg, Thousand Oaks, CA (US); Jian Hua Gu, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 193 days.

This patent is subject to a terminal disclaimer.

(21) Appl. No.: 11/847,984

(22) Filed: Aug. 30, 2007

(65) Prior Publication Data

US 2007/0292506 A1    Dec. 20, 2007

Related U.S. Application Data

(63) Continuation of application No. 11/114,473, filed on Apr. 25, 2005, now Pat. No. 7,323,169.

(60) Provisional application No. 60/565,247, filed on Apr. 23, 2004.

(51) Int. Cl.
*A61K 38/02* (2006.01)
*A61K 38/03* (2006.01)
*A61K 38/08* (2006.01)
*A61K 47/14* (2006.01)

(52) U.S. Cl. .............. 514/2; 514/15; 514/785

(58) Field of Classification Search .............. None
See application file for complete search history.

(56) References Cited

U.S. PATENT DOCUMENTS

| | | | |
|---|---|---|---|
| 2,849,370 A * | 8/1958 | Petersen et al. ............... 514/4 |
| 5,019,400 A | 5/1991 | Gombotz et al. |
| 5,151,265 A * | 9/1992 | Hwang-Felgner et al. .. 424/85.5 |
| 5,192,741 A | 3/1993 | Orsolini et al. |
| 5,916,597 A | 6/1999 | Lee et al. |
| 5,922,253 A | 7/1999 | Herbert et al. |
| 5,962,522 A | 10/1999 | Wacher et al. |
| 5,981,474 A | 11/1999 | Manning et al. |
| 6,180,666 B1 | 1/2001 | Wacher et al. |
| 6,428,818 B1 | 8/2002 | Morre et al. |
| 6,531,154 B1 | 3/2003 | Mathiowitz et al. |
| 6,613,358 B2 | 9/2003 | Randolph et al. |
| 6,759,064 B2 | 7/2004 | Morre et al. |
| 7,323,169 B2 * | 1/2008 | Goldenberg et al. ..... 424/130.1 |
| 2002/0119946 A1 | 8/2002 | Gen |
| 2002/0151582 A1 | 10/2002 | Dou et al. |
| 2003/0190307 A1 * | 10/2003 | DiBiase et al. ............. 424/85.6 |
| 2004/0142048 A1 | 7/2004 | Moore et al. |
| 2005/0180925 A1 * | 8/2005 | Chaudry ...................... 424/46 |
| 2005/0215470 A1 | 9/2005 | Ng et al. |

FOREIGN PATENT DOCUMENTS

| | | |
|---|---|---|
| GB | 929405 A | 6/1963 |
| GB | 1234805 A | 6/1971 |
| WO | WO 94/08599 | 4/1994 |
| WO | WO 98/10649 | 3/1998 |
| WO | WO 99/04764 | 2/1999 |
| WO | WO 00/51643 | 9/2000 |
| WO | WO 01/32218 | 5/2001 |
| WO | WO 2004/012522 | 2/2004 |

OTHER PUBLICATIONS

Yan et al. Identification of histatins as tannin-binding proteins in human saliva. Biochemical Journal. 1995, vol. 311, pp. 341-347.*
Charlton, A. J. et al., "Polyphenol/Peptide Binding and Precipitation," *J. Agric. Food Chem.*, 50, pp. 1593-1601 (2002); published by American Chemical Society.
Chasin, M., "Biodegradable Polymers for Controlled Drug Delivery," J.O. Hollinger Editor, Biomedical Applications of Synthetic Biodegradable Polymers CRC, Boca Raton, FL (1995), pp. 1-15.
Hatano, et al., "Size Exclusion Chromatographic Analysis of Polyphenol-Serum Albumin Complexes," Phytochemistry, 2003, vol. 63, pp. 817-823.
Hyashi, T., "Biodegradable Polymers for Biomedical Uses," Prog. Polym. Sci 19:4 (1994), pp. 663-700.
Matsuo, A. et al., "Interaction of Peptides Having a Turn Structure with Tannins," *Peptide Science 2001*, pp. 205-206, H. Aoyagi (Ed.); The Japanese Peptide Society (2002).
Naurato, et al., "Interaction of Tannin with Human Salivary Histatins," Journal of Agricultural and Food Chemistry, May 4, 1999, vol. 47, No. 6, pp. 2229-2234.
Tamber, H. et al., "Formulation Aspects of Biodegradable Polymeric Microspheres for Antigen Delivery," Advanced Drug Delivery Reviews, 57:3 (2005) pp. 351-376.
Zhang, Y.-J. et al., "Association of Tannins and Related Polyphenols with the Cyclic Peptide Gramicidin S," *Chem. Pharm. Bull.*, 50(2), pp. 258-262 (2002); published by Pharmaceutical Society of Japan.

* cited by examiner

*Primary Examiner*—Jeffrey E Russel
(74) *Attorney, Agent, or Firm*—Nisan A. Steinberg

(57) ABSTRACT

The present invention relates broadly to the field of sustained release formulations. More specifically, the invention describes compositions and methods relating to formulating proteins and/or peptides with purified gallic acid esters. In one example, the gallic acid ester is PentaGalloylGlucose (PGG) and in anther example the gallic acid ester is epigallocatechin gallate (EGCG).

21 Claims, No Drawings

US 7,732,399 B2

SUSTAINED RELEASE FORMULATIONS

This application is a continuation of U.S. patent application Ser. No. 11/114,473, filed Apr. 25, 2005, which issued as U.S. Pat. No. 7,323,169 on Jan. 29, 2008, which in turn claims priority to Provisional Application Ser. No. 60/565,247, filed Apr. 23, 2004, the entire contents of which are incorporated by reference herein.

FIELD OF THE INVENTION

The present invention relates broadly to the field of sustained release formulations. More specifically, the invention describes compositions and methods relating to formulating proteins and/or peptides with purified gallic acid esters. In one example, the gallic acid ester is PentaGalloylGlucose (PGG), where gallic acid is also known as 3,4,5 trihydroxybenzoic acid and in another example the gallic acid ester is epigallocatechin gallate (EGCG).

BACKGROUND

To achieve continuous delivery of the protein or peptide in vivo, a sustained release or sustained delivery formulation is desirable to avoid the need for repeated administrations. One approach for sustained drug delivery is by microencapsulation, in which the active ingredient is enclosed within a polymeric membrane to produce microparticles.

It has been shown that one can encapsulate a biologically active or pharmaceutically active agent within a biocompatible, biodegradable wall forming material such as a polymer, to provide sustained or delayed release. In these methods the agent or drug is typically dissolved, dispersed or emulsified, using stirrers, agitators, or other dynamic mixing techniques, in one or more solvents containing the wall forming material. The solvent is then removed resulting in the formation of microparticles encapsulating the agent or drug. These microparticles can then be administered to a patient.

The importance of biocompatible and/or biodegradable polymers as carriers for parenteral drug delivery systems is now well established. Biocompatible, biodegradable, and relatively inert substances such as poly(lactide) (PLA) or poly(lactide-co-glycolide) (PLGA) microspheres or films containing the active agent to be administered are commonly utilized sustained-release devices (for review, see M. Chasin, Biodegradable polymers for controlled drug delivery. In: J. O. Hollinger Editor, *Biomedical Applications of Synthetic Biodegradable Polymers* CRC, Boca Raton, Fla. (1995), pp. 1-15; T. Hayashi, Biodegradable polymers for biomedical uses. *Prog. Polym. Sci.* 19 4 (1994), pp. 663-700; and Harjit Tamber, Pål Johansen, Hans P. Merkle and Bruno Gander, Formulation aspects of biodegradable polymeric microspheres for antigen delivery *Advanced Drug Delivery Reviews, Volume 57, Issue 3,* 10 *Jan.* 2005, *Pages* 357-376).

However, there still exist many challenges to the design of delivery systems for active agents. A basic requirement for such delivery systems is that the materials used are acceptable for parenteral application. As mentioned above, it is desirable that the materials used are biodegradable for formulations intended for repeated administration. Another generally desirable quality is biocompatibility: the materials should be tolerated well and biodegradation should produce innocuous compounds that are either eliminated from the body or incorporated in the intermediary metabolism. The list of materials used generally for manufacture of parenteral preparations is limited and is shorter still for parenteral protein formulations.

Another desirable attribute is sufficiently good control of the release of the encapsulated active agent. It is generally important to maintain the concentration of the active agent within an effective window for a time period sufficient to achieve the desired effect and to avoid excessive concentrations, which may lead to side effects or untoward results. It is often difficult to achieve the desired release kinetics with monolithic microparticles as the fraction of the active agent released within the first day after administration is often dependent on the loading level of the drug.

Yet another desirable characteristic of sustained delivery technologies, particularly when applied to the delivery of macromolecules, is that the integrity of the active agent is maintained during manufacture. This is often a difficult challenge as most protein and peptide drugs are dependent on a three dimensional conformation for their bioactivity and that conformation can easily be compromised. For example, most of the polymers that are used to manufacture controlled release parenteral preparations are not soluble in water and consequently the protein or peptide is exposed to an organic solvent in the encapsulation step. Examples of other undesirable stresses that are associated with manufacturing of controlled release preparations that may compromise the integrity of any particular active agent are high shear forces used to form droplets of the polymer solution in an continuous phase, exposure to polymerization reactions, high temperatures and undesirably low or high pH values.

Another desirable attribute of sustained release modalities is that the integrity of the active agent, particularly proteins or peptides, is retained within the microparticles during release. Depending on the chosen duration of release, this period can be from a few days up to several months. For conventional polymer matrix systems formed of PLGA the acidic microenvironment formed during biodegradation of the polymer may degrade active agents incorporated therein during in vitro and in vivo incubation.

The prior art describes various sustained delivery compositions and methods for making them, for example, U.S. Pat. Nos. 5,916,597; 5,019,400; 5,922,253; and 6,531,154. The in vivo release of incorporated active agents from biocompatible and biodegradable polymers is, in many cases, initially high or low, and therefore non-uniform throughout the life of the delivery device. Additionally, microencapsulation with polymers tends to provide long term sustained delivery of peptides ranging from two weeks to nine months or longer whereas there is a need for shorter term delivery profiles for certain medicaments. Thus, there is a need in the art for sustained release compositions with release profiles of less than about a week or two.

SUMMARY OF THE INVENTION

The present invention provides pharmaceutical compositions comprising a stable sustained release complex composed of a protein and/or peptide and a gallic acid ester that allow for sustained delivery of the protein or peptide in vivo upon administration of the complex. Accordingly, the complex of the invention can permit continuous delivery of a pharmaceutically active peptide to a subject for periods of time less than about one or two weeks.

The complex of the invention is formed by combining a protein or peptide and a gallic acid ester under conditions such that a complex is formed. In a preferred embodiment, the complex is a salt of the gallic acid ester and protein or peptide. The complex is typically poorly soluble in water and can be purified from various aqueous solutions. As the complex is in the form of a solid (e.g., a paste, granules, a powder or a lyophilizate), the complex can be prepared for administration to a subject as a stable liquid suspension or semi-solid dispersion.

In one embodiment of the invention, the group suitable for use in forming a complex with a peptide or protein is a gallic acid ester. Preferably, the ester itself is formed by a linkage of the acid group of gallic acid to an alcohol moiety on another compound such as a sugar. In a particular embodiment, the gallic acid ester is PentaGalloylGlucose (PGG), where the gallic acid is also known as 3,4,5-trihydroxybenzoic acid. In another embodiment, the gallic acid ester is Epigallocatechin Gallate (EGCG).

DETAILED DESCRIPTION

The present invention relates to compositions comprising a sustained release complex composed of a protein or peptide and a gallic acid ester, methods of making such compositions and methods of using such compositions. While gallic acid esters are a known component of tannic acid, the use of a highly purified component of tannic acids such as particular gallic acid esters to make a salt with peptides and polypeptides to create a sustained release formulation as described herein, has not been described. The advantages of the compositions of the invention include the delivery of the peptide or protein portion of the complex, either systemically or locally, for a controlled periods (e.g., typically less than about one or two weeks). Delivery for longer periods of time is also contemplated.

As used herein, the terms "protein" and "peptide" are understood to include polymers of amino acids linked by amide bonds. Typically, a peptide will be composed of less than about 50 amino acids, more typically less than about 30 amino acid residues and even more typically, less than about 20 amino acid residues. Whereas a protein will typically be composed of more than 50 amino acids and will have structure and biological activity. The protein's biological activity can be enzymatic or it may be a binding activity that confers conformation changes. These terms are further intended to encompass analogues and derivatives that mimic the chemical structure of the components of the protein or peptides. Examples of analogues include peptides or proteins containing one or more non-natural amino acids. Examples derivatives include peptides or proteins containing amino acid side chain(s), peptide backbone, and/or amino- or carboxy-terminus that have been derivatized.

Peptides suitable for formulation according to the invention include but are not limited to enfuvirtide (sold by Trimeris and Roche as Fuzeon®), Angiotensin, Amylin, ACTH, renin substrate, Cecropin A-Melittin amide, Cecropin B, Magainin 1, Renin Inhibitor Peptide, Bombesin, Osteocalcin, Bradykinin, B1 Inhibitor Peptide, Bradykinin peptide antagonists, including bradykinin peptide antagonists disclosed in U.S. patent application Ser. No. 10/972,236, filed on Oct. 21, 2004, Kallidin, Calcitonin, Cholecystokinin, Corticotropin Releasing Factor, Dynorphin A, Endomorphin, Sarafotoxin, Enkephalin, Exendin, Fibrinopeptide, Galanin, Gastrin, Gastrin Releasing Peptide, Glucagon-Like Peptide, Growth Hormone Releasing Factor, OVA Peptide, Luteinizing Hormone-Releasing Hormone, Atrial Natriuretic Peptide, Melanin Concentrating Hormone, Brain Natriuretic Peptide, Vasonatrin, Neurokinin, Neuromedin, Neuropeptide Y, Neurotensin, Orexin, Oxytocin, Vasopressin, Parathyroid Hormone Peptide, Prolactin Releasing Peptide, Somatostatin, Somatostatin Tumor Inhibiting Analog, Thyrotropin Releasing Hormone, and variants and derivatives thereof (see also, Latham, (1999) Nat. Biotech., 17:755).

Proteins that can be formulated according to the invention include but are not limited to Flt3 ligand, CD40 ligand, erythropoietin, thrombopoeitin, calcitonin, Fas ligand, ligand for receptor activator of NF-kappa B (RANKL), TNF-related apoptosis-inducing ligand (TRAIL), ORK/Tek, thymic stroma-derived lymphopoietin, granulocyte colony stimulating factor, granulocyte-macrophage colony stimulating factor, mast cell growth factor, stem cell growth factor, epidermal growth factor, RANTES, growth hormone, insulin, insulinotropin, insulin-like growth factors, parathyroid hormone, nerve growth factors, glucagon, interleukins 1 through 18, colony stimulating factors, lymphotoxin-β, tumor necrosis factor, leukemia inhibitory factor, oncostatin-M, and various ligands for cell surface molecules Elk and Hek (such as the ligands for eph-related kinases, or LERKS). Descriptions of making such proteins may be found in, for example, Human Cytokines: Handbook for Basic and Clinical Research, Vol. II (Aggarwal and Gutterman, Eds. Blackwell Sciences, Cambridge Mass., 1998); Growth Factors: A Practical Approach (McKay and Leigh, Eds. Oxford University Press Inc., New York, 1993) and The Cytokine Handbook (AW Thompson, ed.; Academic Press, San Diego Calif.; 1991).

Receptors for any of the aforementioned proteins can also be formulated according to the invention, provided that they are soluble portions of the molecule suitable for administration to a subject. Examples include the receptors for both forms of tumor necrosis factor receptor (referred to as p55 and p75), Interleukin-1 receptors (type 1 and 2), Interleukin-4 receptor, Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK), receptors for TRAIL, and receptors that comprise death domains, such as Fas or Apoptosis-Inducing Receptor (AIR). A particularly preferred receptor is a soluble form of the IL-1 receptor type II; such proteins are described in U.S. Pat. No. 5,767,064, incorporated herein by reference in its entirety.

Other proteins that can be formulated according to the invention include soluble variants of cluster of differentiation antigens (referred to as CD proteins), for example, those disclosed in Leukocyte Typing VI (Proceedings of the VIth International Workshop and Conference; Kishimoto, Kikutani et al., Eds. Kobe, Japan, 1996), or CD molecules disclosed in subsequent workshops. Examples of such molecules include CD27, CD30, CD39, CD40; and ligands thereto (CD27 ligand, CD30 ligand and CD40 ligand). Several of these are members of the TNF receptor family, which also includes 41BB and OX40; the ligands are often members of the TNF family (as are 41BB ligand and OX40 ligand); accordingly, members of the TNF and TNFR families can also be produced using the present invention.

Enzymatically active proteins can also be formulated according to the invention. Examples include metalloproteinase-disintegrin family members, various kinases, glucocerebrosidase, alpha-galactosidase A, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, and numerous other enzymes. Ligands for enzymatically active proteins can also be formulated by applying the instant invention.

The inventive compositions and methods are also useful for formulation of other types of proteins, including immunoglobulin molecules or portions thereof, and chimeric antibodies (i.e., an antibody having a human constant region couples to a murine antigen binding region) or fragments thereof. Numerous techniques are known by which DNA encoding immunoglobulin molecules can be manipulated to yield DNAs capable of encoding recombinant proteins such as single chain antibodies, antibodies with enhanced affinity, or other antibody-based proteins (see, for example, Larrick et al., 1989, Biotechnology 7:934-938; Reichmann et al., 1988, Nature 332:323-327; Roberts et al., 1987, Nature 328:731-734; Verhoeyen et al., 1988, Science 239:1534-1536; Chaudhary et al., 1989, Nature 339:394-397). The term humanized antibody also encompasses single chain antibodies. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. For example, the invention can be used to formulate human and/or humanized antibodies that immunospecifically recognize specific cellular targets, e.g., any of the aforementioned proteins, the human EGF receptor, the her-2/neu antigen, the CEA antigen, Prostate Specific Membrane Antigen (PSMA), CD5, CD11a, CD18, NGF, CD20, CD45, Ep-cam, other cancer cell surface molecules, TNF-alpha, TGF-beta1, VEGF, other cytokines, alpha 4 beta 7 integrin, IgEs, viral proteins (for example, cytomegalovirus), etc., to name just a few.

Various fusion proteins can also be formulated according to the invention. A fusion protein is a protein, or domain or a protein (e.g. a soluble extracellular domain) fused to a heterologous protein or peptide. Examples of such fusion proteins include proteins expressed as a fusion with a portion of an immunoglobulin molecule, proteins expressed as fusion proteins with a zipper moiety, and novel polyfunctional proteins such as a fusion proteins of a cytokine and a growth factor (i.e., GM-CSF and IL-3, MGF and IL-3). WO 93/08207 and WO 96/40918 describe the preparation of various soluble oligomeric forms of a molecule referred to as CD40L, including an immunoglobulin fusion protein and a zipper fusion protein, respectively; the techniques discussed therein are applicable to other proteins. Another fusion protein is a recombinant TNFR:Fc, also known as "etanercept." Etanercept is a dimer of two molecules of the extracellular portion of the p75 TNF alpha receptor, each molecule consisting of a 235 amino acid TNFR-derived protein that is fused to a 232 amino acid Fc portion of human IgG1. In fact, any of the previously described molecules can be expressed as a fusion protein including but not limited to the extracellular domain of a cellular receptor molecule, an enzyme, a hormone, a cytokine, a portion of an immunoglobulin molecule, a zipper domain, and an epitope.

As used herein, the term "gallic acid ester" is intended to refer to a molecule that can complex with a protein or peptide to form a sustained release complex. In one example, the gallic acid ester molecule is a PentaGalloylGlucose (PGG, also referred to in the art as 5GG). It is understood that the PGG molecule can have one galloyl group, two galloyl groups, three galloyl groups or four galloyl groups. In addition, it is understood that glucose can be replaced with another carbon backbone, such as an alcohol or polyol, e.g., glycerol, ethylene glycol or any sugar group suitable for use. In another example, Epigallocatechin Gallate (EGCG) is the gallic acid ester molecule useful in the invention to make a salt with a peptide or protein. EGCG is an anti-oxidant polyphenol flavonoid isolated from green tea. The EGCG ester is attached to a ring structure that is not a sugar, in contrast to PGG. Further, it is understood that the gallic acid ester can assume different stereochemical forms. For example, PGG can be in either alpha or beta forms. One of skill in the art will be able, for the teachings herein, to identify appropriate gallic acid ester molecules for use in the compositions and methods of the invention.

As used herein, the term "sustained release complex" is intended to refer to a physically and chemically stable complex that forms upon appropriate combining of a protein or peptide and gallic acid ester described herein. This complex typically takes the form of a precipitate that is produced upon combining aqueous or non-aqueous preparations of the protein or peptide and gallic acid ester.

As used herein, the term "sustained delivery" is intended to refer to continual delivery of a pharmaceutical agent in vivo over a period of time following administration. Sustained delivery of the agent can be demonstrated by, for example, the continued therapeutic effect of the agent over time. Alternatively, sustained delivery of the agent may be demonstrated by detecting the presence of the agent in vivo over time. In one embodiment, the sustained delivery is less than a week and can be less than four days. However, it is also contemplated that the sustained delivery can be for periods longer than one week using the compositions of the invention, including more than two weeks.

The formation of a PGG or EGCG complex with a peptide or protein at different pH's can affect the period of drug delivery. As shown below in Examples 4 and 5, formation of a PGG complex with a peptide at pH 7.0 results in longer duration in serum of the complex, i.e., about a week, than those complexes formed at pH 7.6 and pH 8.6, i.e., less than a week. Thus, it is an embodiment of the invention that the duration of drug delivery is controlled in part by the pH at which the complex is formed. A representative pH range is 6.0 to 9.0, and the ranges of pH 6.5 to 8.6, pH 7.0 to 8.6 are also suitable. One of skill in the art would readily understand that other pH's may be suitable and given the teachings of the invention, it is no more than routine experimentation to determine what pH best suits the desired drug delivery profile of a particular drug complexed with the tannic acid esters of the invention.

One aspect of the present invention pertains to a pharmaceutical composition comprising a sustained release complex of a pharmaceutically active agent such as a protein or peptide and a gallic acid ester. The pharmaceutical compositions of the invention permit sustained delivery of a protein or peptide to a subject in vivo after administering the composition to the subject, wherein the duration of the sustained delivery can be varied depending upon the solubility of peptide and gallic acid ester complex. For example, in one embodiment, the sustained release complex provides sustained delivery of a pharmaceutically active agent to a subject for at less than one week after a pharmaceutical composition of the invention is administered to the subject. In another embodiment, the sustained release complex provides sustained delivery of a protein or peptide to a subject for less than four days. Formulations that provide sustained delivery for longer or shorter durations are also encompassed by the invention, such as formulations that provide continuous delivery for 1 day, 2 days, 3 days, 4 days, 5 days, 6 days or a week and the like. Likewise, it is contemplated that these compositions can be formulated such that they provide continuous drug delivery for over one week, and up to two weeks, or more.

Any size amino acid chain may be suitable for use in the complex as long as the protein or peptide has the ability to form a sustained release noncovalent complex with the gallic acid ester upon combination of the two.

In addition to the sustained release complex, the pharmaceutical formulations of the invention can comprise additional pharmaceutically acceptable carriers and/or excipients. As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous or parenteral administration (e.g., by injection). Excipients include pharmaceutically acceptable stabilizers and disintegrants.

In addition to pharmaceutical formulations of peptides complexed with a gallic acid ester, the invention further encompasses packaged formulations containing such complexes and syringes containing such complexes. In another embodiment, the invention provides a syringe having a lumen, wherein a sustained release complex of a protein or peptide and a gallic acid ester is included in the lumen.

The complex of the invention is prepared by combining the protein or peptide and the gallic acid ester under conditions such that a sustained release complex of the protein or peptide and the gallic acid ester forms. Accordingly, another aspect of the invention pertains to methods for preparing pharmaceutical formulations. In one embodiment, the method comprises providing a protein or peptide and a gallic acid ester, combining the protein or peptide and the gallic acid ester under conditions such that a complex of the protein or peptide and the gallic acid ester forms, and preparing a pharmaceutical formulation comprising the complex.

For example, a solution of the protein or peptide and a solution of the gallic acid ester are combined until a sustained release complex of the protein or peptide and the gallic acid ester precipitates out of solution. In certain embodiments, the solutions of the protein or peptide and the gallic acid ester are aqueous solutions. The amounts of protein or peptide and gallic acid ester necessary to achieve the sustained release complex may vary depending upon the particular protein or peptide and gallic acid ester used, the particular solvent(s) used and/or the procedure used to achieve the complex. Often, the protein or peptide also will be in excess on a weight/weight basis, as demonstrated in the Examples.

Once the protein or peptide/gallic acid ester complex precipitates out of solution, the precipitate can be removed from the solution by means known in the art, such as filtration, centrifugation and the like. The recovered material then can be dried and the solid can be milled or pulverized to a powder by means known in the art. Alternatively, the paste can be frozen and lyophilized to dryness. The powder form of the complex can be dispersed in a carrier solution to form a liquid suspension or semi-solid dispersion suitable for injection. Accordingly, in various embodiments, a pharmaceutical formulation of the invention is a lyophilized solid, a liquid suspension or a semi-solid dispersion.

In another embodiment, the pharmaceutical formulation of the invention is sterile formulation. For example, following formation of the sustained release complex, the complex can be sterilized by gamma irradiation or electron beam sterilization. Pharmaceutical formulations, including powders, liquid suspensions, semi-solid dispersions, lyophilized solids, and sterilized forms thereof (e.g., by gamma irradiation or sterile filtration), prepared according to the methods of the invention, are also encompassed by the invention.

As used herein, the term "subject" is intended to include is intended to include warm-blooded animals, preferably mammals, most preferably humans.

As used herein, the term "administering to a subject" is intended to refer to dispensing, delivering or applying a composition (e.g., pharmaceutical formulation) to a subject by any suitable route for delivery of the composition to the desired location in the subject, including delivery by either the parenteral or oral route, intramuscular injection, subcutaneous/intradermal injection, intravenous injection, buccal administration, transdermal delivery and administration by the rectal, colonic, vaginal, intranasal or respiratory tract route.

The following examples are merely representative embodiments and not meant to be limiting as to the full scope of the invention.

Example 1

Example 1 provides a description of a preparation of Peptide B-PGG salt (1:1 molar ratio of Peptide B (DOrn Lys Arg Pro Hyp Gly Cpg Ser Dtic Cpg) to PGG). A stock solution of PGG was made by dissolving 94 mg of PGG in 2 ml of NaOH solution (concentration of NaOH from 0.10 to 0.20 N) following by filtering it through a 0.2 um filter. To a stock solution of PGG (1.56 mL) was added sequentially a solution of 109.4 mg of Peptide B acetate salt in 0.8 mL water with stirring and a precipitate formed. The precipitate was recovered by centrifugation.

The supernatant was decanted and the precipitate was washed with 0.5 mL water 3 times. The precipitate was dried in vacuum at approximately 30-35° C. for approximately 20 hours to yield 125 mg (76%). The Peptide B-PGG salt was an off-white powder.

Example 2

Salts of Peptide A-PGG and tannate were made in a similar way to Peptide B-PGG in Example 1. Peptide A was Acetyl Lys Lys Arg Pro Hyp Gly Cpg Ser Dtic Cpg.

Example 3

The tables 1 and 2 below list peptide content and solubility of Peptide A (Acetyl Lys Lys Arg Pro Hyp Gly Cpg Ser Dtic Cpg) and Peptide B (DOrn Lys Arg Pro Hyp Gly Cpg Ser Dtic Cpg) salts with tannate and PGG in water and PBS. The data showed that the PGG peptide salt has higher peptide content than the tannate. The PGG precipitates have higher PBS solubility than the tannate.

Example 4

The study of the effect of salt formation pH (i.e. concentration level of NaOH) on the yield, peptide content and solubility of Peptide B-PGG salt was investigated. Four Peptide B-PGG salts at pH 7.0, 7.2, 7.6 and 8.6 were prepared and isolated. Their solubility in water and PBS, and also their peptide content were then determined. These results demonstrate (Table 3) that aqueous solubility, yield of salt formation and peptide content increase with increasing pH during salt formation.

Example 5

This example describes sustained release of Peptide B/PGG and Peptide B/tannate salts in rats. The rat pharmacokinetics (PK) studies were performed by a single subcutaneous injection (10 mg/kg dose) of Peptide B/PGG salts and Peptide B/tannate salt suspended in TRIS buffer; and a PBS solution of Peptide B acetate as a control group. The PK results showed one-week sustained release for Peptide B/tannate salt and Peptide B-PGG salt that prepared at pH 7.0. However, Peptide B-PGG salts prepared at pH 7.6 and 8.6 showed shorter release duration (around 2-3 days) compared to salt prepared at pH 7.0 (up to two weeks).

Example 6

A pure anomer (beta-PGG) and a mixture of anomers (alpha+beta-PGG) of PGG salts of Peptide B (DOrn Lys Arg Pro Hyp Gly Cpg Ser Dtic Cpg) were prepared by a similar method to that described in Example 1. There was no significant difference in the aqueous solubility of these salts. Based on aqueous solubility, it is expected that the in vivo sustained release duration for these salts would be similar.

Example 7

The following example describes the use of EGCG to make a salt with a peptide, which was tested in an animal pharmacokinetic (PK) study for sustained release. A stock solution of EGCG (Sigma-Aldrich) was made by dissolving 184 mg of EGCG in 2 ml of 0.2 N NaOH followed by filtering it through a 0.2 um filter. To a stock solution of EGCG (1.4 mL) was slowly added a solution of 138 mg of acetate salt of Peptide B (DOrn Lys Arg Pro Hyp Gly Cpg Ser Dtic Cpg) in 1.2 mL water with stirring. The resulting suspension was stirred for approximately 10-15 minutes at room temperature. After centrifugation, the supernatant was decanted and the precipitate was washed with 1 mL water (3 times by centrifugation and decantation of supernatant). The precipitate was dried under vacuum at approximately 30-35° C. for approximately 20 hours to yield 218 mg (88%) of Peptide B-EGCG salt as an off-white powder.

The peptide content of the Peptide B/EGCG salts were 47-50%. The aqueous solubility for the salt with 1:3 molar ratio of peptide to EGCG is <0.5 mg/ml in water and <0.05 mg/ml in PBS, and for 1:2 molar ratio of peptide to EGCG, solubility is approximately 1 mg/ml in water and approximately 0.3 mg/ml in PBS. A rat PK study was performed using a single sc injection (10 mg/kg dose) of '593/EGCG salt suspended in TRIS buffer, pH7.0. The PK result showed sustained release of Peptide B for multiple days with the blood level>26 ng/ml at 24 hours, then a decrease to approximately 5 ng/ml at 96 hours.

TABLE 1

Peptide A Precipitates

| Salt name | Yield (%) | Peptide purity (%) | Peptide content (%) | Conjugated salt purity (%) | Peptide solubility (mg/mL) at RT | |
|---|---|---|---|---|---|---|
| | | | | | $H_2O$ | PBS |
| PGG | ~78 | >98 | 50 | >97% ($\alpha + \beta$) | ~0.03 | ~0.2 |
| Tannate | ~75 | >98 | 32 | N/A | ~0.01 | ~0.05 |

TABLE 2

Peptide B Precipitates

| Salt name | Yield (%) | Peptide purity (%) | Peptide content (%) | Conjugated salt purity (%) | Peptide solubility (mg/mL) at RT | |
|---|---|---|---|---|---|---|
| | | | | | H2O | PBS |
| PGG | ~75 | >98 | 44 | >97% ($\alpha + \beta$) | ~0.2 | ~0.08 |
| Tannate | ~75 | >98 | 28 | N/A | ~0.2 | ~0.01 |

TABLE 3

Peptide B precipitates formed at different pH

| Salts | Salt formation condition | | | Yield (%) | Peptide content (%) | Peptide B (mg/ml) | |
|---|---|---|---|---|---|---|---|
| | Conc. of PGG | Conc. of NaOH | pH | | | In $H_2O$ | In PBS |
| Peptide B-PGG | 0.05 M | 0.10 N | 7.0 | Approx. 70 | 46.5 | Approx. 0.2 | Approx. 0.08 |
| Peptide B-PGG | 0.05 M | 0.12 N | 7.2 | Approx. 75 | 50.0 | Approx. 0.1 | Approx. 0.15 |
| Peptide B-PGG | 0.05 M | 0.15 N | 7.6 | Approx. 92 | 53.0 | <0.1 | Approx. 0.2 |
| Peptide B-PGG | 0.05 M | 0.20 N | 8.6 | Approx. 96 | 56.5 | | Approx. 0.4 |

While the present invention has been described in terms of preferred embodiments, it is understood that variations and modifications will occur to those skilled in the art. Therefore, it is intended that the appended claims cover all such equivalent variations which come within the scope of the claims.

Each of the patents, applications and articles cited hereinabove (hereinafter, "references"), and each document cited or referenced therein, including during the prosecution of any of the patents and/or applications cited herein ("patent cited documents"), and any manufacturer's instructions or catalogues for any products cited herein or mentioned in any of the references and in any of the patent cited documents, are hereby incorporated herein by reference. Furthermore, all documents cited in this text, and all documents cited or referenced in documents cited in this text, and any manufacturer's instructions or catalogues for any products cited or mentioned in this text or in any document hereby incorporated into this text, are hereby incorporated herein by reference. Documents incorporated by reference into this text or any teachings therein may be used in the practice of this invention. Documents incorporated by reference into this text are not admitted to be prior art.

What is claimed is:

1. A pharmaceutical formulation comprising: a sustained release complex of a peptide of 20 amino acids or less, wherein said peptide is a B1 antagonist, and a purified gallic acid ester; and a pharmaceutically acceptable carrier or excipient, or both.

2. The formulation of claim 1, wherein the complex is a salt of the peptide and the gallic acid ester.

3. The formulation of claim 1, wherein the gallic acid ester is selected from the group consisting of PentaGalloylGlucose (PGG) and epigallocatechin gallate (EGCG).

4. The formulation of claim 3 wherein the purified gallic acid ester is PentaGalloylGlucose (PGG).

5. The formulation of claim 4, wherein the complex is a salt of the peptide and PGG, and the salt has a release duration in an animal of less than one week or about one week.

6. The formulation of claim 4, wherein the complex is a salt of the peptide and PGG, and the salt has a release duration in an animal of less than 4 days.

7. The formulation of claim 3 wherein the purified gallic acid ester is epigallocatechin gallate (EGCG).

8. The formulation of claim 1 wherein the peptide in the complex is in excess of the purified gallic acid ester on a weight/weight basis.

9. The formulation of claim 1 wherein the molar ratio of peptide to purified gallic acid ester is 1:1, 1:2, or 1:3.

10. The formulation of claim 4, wherein the complex is a salt of the peptide and PGG, and the salt has a release duration in an animal of up to two weeks.

11. The formulation of claim 1 wherein said peptide is selected from i) DOrn Lys Arg Pro Hyp Gly Cpg Ser Dtic Cpg; and ii) Acetyl Lys Lys Arg Pro Hyp Gly Cpg Ser Dtic Cpg wherein DOrn is the 0 isomer of ornithine, Hyp is Trans-4-hydroxy-proline, Dtic is the D isomer of 1,2,3,4-tetrahydroisoquinoline-3-carboxylic acid, and Cpg is cyclopentylglycine.

12. The formulation of claim 3 wherein said peptide is selected from i) DOrn Lys Arg Pro Hyp Gly Cpg Ser Dtic Cpg; and ii) Acetyl Lys Lys Arg Pro Hyp Gly Cpg Ser Dtic Cpg wherein DOrn is the D isomer of ornithine, Hyp is Trans-4-hydroxy-proline, Dtic is the D isomer of 1,2,3,4-tetrahydroisoquinoline-3-carboxylic acid, and Cpg is cyclopentylglycine.

13. A method of making the pharmaceutical formulation of claim 1 comprising combining the peptide with a purified gallic acid ester under conditions such that a complex of the peptide and purified gallic acid ester forms, and preparing a pharmaceutical formulation comprising the complex.

14. The method of claim 13, wherein a solution of the peptide and a solution of the gallic acid ester are combined and the complex precipitates out of the combined solution.

15. The method of claim 13, wherein the complex is formed at a pH from 6.5 to 8.6.

16. The method of claim 13 wherein the gallic acid ester is PGG.

17. The method of claim 13 wherein the gallic acid ester is EGCG.

18. A method of making a pharmaceutical formulation comprising combining a peptide of 20 amino acids or less with epigallocatechin gallate (EGCG) under conditions such that a complex of the peptide and EGCG forms at a pH from 6.0 to 9.0, and preparing a pharmaceutical formulation comprising the complex.

19. The method of claim 18, wherein a solution of the peptide and a solution of the EGCG are combined and the complex precipitates out of the combined solution.

20. A pharmaceutical formulation, comprising:
a sustained release complex of a peptide of 20 amino acids or less, wherein said peptide is a B1 antagonist, and a purified gallic acid ester selected from PentaGalloylGlucose (PGG) and epigallocatechin gallate (EGCG); and
a pharmaceutically acceptable carrier suitable for subcutaneous administration.

21. A method of making the pharmaceutical formulation of claim 20, comprising: combining the peptide with a purified gallic acid ester selected from PentaGalloylGlucose (PGG) and epigallocatechin gallate (EGCG), under conditions such that a complex of the peptide and purified gallic acid ester forms, and preparing a pharmaceutical formulation comprising the complex and a pharmaceutically acceptable carrier suitable for subcutaneous administration.

* * * * *